United States Patent
Gatzemeyer et al.

(10) Patent No.: US 10,398,538 B2
(45) Date of Patent: *Sep. 3, 2019

(54) METHOD OF MONITORING ORAL HEALTH

(71) Applicant: COLGATE-PALMOLIVE COMPANY, New York, NY (US)

(72) Inventors: John J. Gatzemeyer, Hillsborough, NJ (US); Elizabeth K. Gittins, Stewartsville, NJ (US); Eduardo Jimenez, Manalapan, NJ (US); Sharon Kennedy, Randallstown, MD (US); Harsh M. Trivedi, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 597 days.

This patent is subject to a terminal disclaimer.

(21) Appl. No.: 14/709,140

(22) Filed: May 11, 2015

(65) Prior Publication Data

US 2015/0257863 A1 Sep. 17, 2015

Related U.S. Application Data

(63) Continuation of application No. 12/142,136, filed on Jun. 19, 2008, now Pat. No. 9,072,370.

(51) Int. Cl.
*A61B 5/00* (2006.01)
*A61C 19/04* (2006.01)
(Continued)

(52) U.S. Cl.
CPC .......... *A61C 19/04* (2013.01); *A46B 15/0002* (2013.01); *A46B 15/0004* (2013.01);
(Continued)

(58) Field of Classification Search
CPC combination set(s) only.
See application file for complete search history.

(56) References Cited

U.S. PATENT DOCUMENTS 5,894,620 A     4/1999  Polaert et al.
5,944,531 A *   8/1999  Foley ................. G09B 19/0084
                                                      434/262

(Continued)

FOREIGN PATENT DOCUMENTS

DE    100 45 067    4/2002
EP     0 097 904    1/1984
(Continued)

OTHER PUBLICATIONS

International Search Report issued in International Application PCT/US2008/067607 dated Dec. 17, 2008.

(Continued)

*Primary Examiner* — Christopher A Flory
*Assistant Examiner* — Shirley X Jian

(57) ABSTRACT

A method of monitoring oral health including deriving a health profile of a user from information obtained from a sample taken from the user; displaying a representation of the health profile on a display, wherein the representation of the health profile includes a list of undesirable oral health characteristics that are detectable from the sample and a graphical depiction of an oral cavity divided into a plurality of regions; and wherein in response to selection of a first one of the undesirable oral health characteristics, the representation of the health profile indicates which regions of the user's oral cavity are affected by the first one of the undesirable oral health characteristic.

19 Claims, 5 Drawing Sheets

(51) Int. Cl.

| | | |
|---|---|---|
| *A46B 15/00* | (2006.01) | |
| *A61B 5/0205* | (2006.01) | |
| *A61B 5/145* | (2006.01) | |
| *A61B 10/00* | (2006.01) | |
| *G16H 10/60* | (2018.01) | |

(52) U.S. Cl.
CPC ...... *A46B 15/0006* (2013.01); *A46B 15/0008* (2013.01); *A46B 15/0012* (2013.01); *A46B 15/0014* (2013.01); *A46B 15/0055* (2013.01); *A61B 5/0205* (2013.01); *A61B 5/14507* (2013.01); *A61B 5/14539* (2013.01); *A61B 5/14546* (2013.01); *A61B 10/0051* (2013.01); *G16H 10/60* (2018.01); *A46B 2200/1066* (2013.01)

(56) References Cited

U.S. PATENT DOCUMENTS

| | | | | |
|---|---|---|---|---|
| 6,116,910 | A * | 9/2000 | Green | G09B 23/283 273/117 |
| 6,485,300 | B1 | 11/2002 | Muller et al. | |
| 6,536,068 | B1 * | 3/2003 | Yang | A46B 15/0002 15/105 |
| 6,611,780 | B2 * | 8/2003 | Lundell | A61C 17/22 433/27 |
| 6,623,698 | B2 * | 9/2003 | Kuo | A61B 10/0051 422/547 |
| 7,343,305 | B2 * | 3/2008 | Benn | A61C 19/00 433/215 |
| 7,386,333 | B1 | 6/2008 | Birecki | |
| 8,972,882 | B2 * | 3/2015 | Berry | G06F 3/04845 434/262 |
| 2002/0127143 | A1 | 9/2002 | Kuo | |
| 2004/0078219 | A1 | 4/2004 | Kaylor et al. | |
| 2005/0039127 | A1 * | 2/2005 | Davis | G06F 19/327 715/708 |
| 2005/0101841 | A9 | 5/2005 | Kaylor et al. | |
| 2005/0221401 | A1 | 10/2005 | Nomura et al. | |
| 2006/0141421 | A1 | 6/2006 | Braunecker et al. | |
| 2006/0225744 | A1 | 10/2006 | Braunecker et al. | |
| 2007/0055481 | A1 * | 3/2007 | Baird | G06F 19/363 702/183 |
| 2008/0060148 | A1 | 3/2008 | Pinyayev et al. | |
| 2008/0109973 | A1 * | 5/2008 | Farrell | A46B 7/04 15/4 |
| 2008/0209050 | A1 | 8/2008 | Li | |
| 2010/0170052 | A1 * | 7/2010 | Ortins | A46B 15/0002 15/106 |
| 2012/0171657 | A1 | 7/2012 | Ortins et al. | |

FOREIGN PATENT DOCUMENTS

| | | | |
|---|---|---|---|
| EP | 0 205 844 | 7/1990 | |
| EP | 0205844 B1 * | 7/1990 | ............... C12Q 1/28 |
| EP | 1 189 550 | 3/2002 | |
| EP | 1 698 252 | 9/2006 | |
| JP | 2004-108858 | 4/2004 | |
| JP | 2005-257604 | 9/2005 | |
| RU | 2234846 | 8/2004 | |
| WO | WO 2006/137648 | 12/2006 | |
| WO | WO 2006/137661 | 12/2006 | |

OTHER PUBLICATIONS

Ojima et al., Development of Web-Based Intervention System for Periodontal Health: A Pilot Study in the Workplace, Med. Inform. Internet Med. 28 (4) 2003, 291-298; Abstract only.

\* cited by examiner

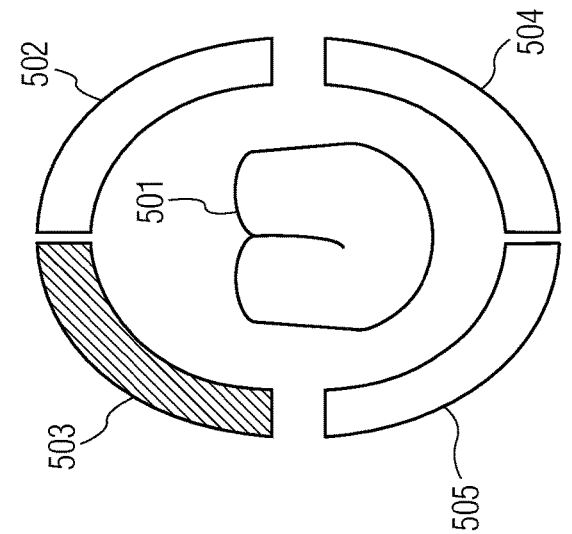

METHOD OF MONITORING ORAL HEALTH

CROSS-REFERENCE TO RELATED APPLICATIONS

The present application is a continuation of U.S. patent application Ser. No. 12/142,136, filed Jun. 19, 2008, the entirety of which is incorporated herein by reference.

BACKGROUND OF THE INVENTION

Tooth brushing is part of a daily oral hygiene activity. Proper dental care involves regular flossing, brushing and dental checkups. According to the American Dental Association, a major source of bad breath in healthy people is microbial deposits on the tongue, where a bacterial coating harbors organisms and debris that contribute to bad breath. Tissue in the mouth, and especially the tongue, is a haven for the growth of microorganisms. Anaerobic flora and bacteria residing on the tongue and other soft tissues in the mouth play a role in the development of chronic bad breath commonly called halitosis. In general, the bacteria produce volatile sulfur compounds (VSC). If there is enough buildup of the sulfur compounds, the result can be bad breath or oral malodor.

Dentists generally recommend that an individual brush his or her teeth for a minimum interval per cleaning, such as two minutes. Despite such recommendations, many individuals, especially young children, do not regularly brush their teeth for the recommended minimum interval. Such habits often can be attributed to the individual regarding tooth brushing as a mundane duty with few pleasurable aspects. Dental checkups to a dentist office are typically the only feedback a person receives on their dental cleaning efforts. There is unfortunately ample time between checkups for poor dental habits to cause problems. For example, gingivitis, periodontal disease, and a host of other problems can be magnified if poor dental cleaning habits are not rectified promptly.

BRIEF SUMMARY OF THE INVENTION

Aspects of the present invention are directed to providing an oral care implement (such as a toothbrush) having an oral care diagnostic feature. Various aspects of the oral care implement may improve dental care by providing feedback on a user's brushing efforts.

Further aspects are directed to providing a health profile to the user based on information from such a diagnostically-capable oral care implement, or a conventional oral care implement. The health profile may be created by analyzing information obtained from the oral care implement and presenting representations of certain health aspects. The health aspects may include indications relating, for example, to whether certain oral or non-oral diseases are suspected, as well as to whether certain brushing techniques are being properly executed. This type of health profile may, in certain circumstances, provide even more information to a user than may be available via feedback provided by the oral care implement itself.

Still further aspects are directed to providing a health profile service business, such as over the Internet and/or through a brick-and-mortar boutique storefront. In such a case, data from the oral care implement, or even the oral care implement itself, may be provided to the health profile service. The service may in turn process the data and/or oral care implement to generate the health profile, which is then provided to the customer/user of the oral care implement.

In one aspect, the invention may be a method of monitoring oral health comprising: deriving a health profile of a user from information obtained from a sample taken from the user; displaying a representation of the health profile on a display, wherein the representation of the health profile includes a list of undesirable oral health characteristics that are detectable from the sample and a graphical depiction of an oral cavity divided into a plurality of regions; and wherein in response to selection of a first one of the undesirable oral health characteristics, the representation of the health profile indicates which regions of the user's oral cavity are affected by the first one of the undesirable oral health characteristic.

In another aspect, the invention may be a method of monitoring oral health comprising: deriving a health profile of a user from information obtained from a sample taken from the user; displaying a representation of the health profile on a user interactive display, wherein the representation of the health profile includes a list of a plurality of undesired oral health characteristics that are detectable from the sample; selecting a first one of the plurality of undesired oral health characteristics on the user interactive display, wherein the user interactive display displays a first advice or instructions for remedying the first one of the plurality of undesired oral health characteristics in response to the selection of the first one of the plurality of undesired oral health characteristics; and selecting a second one of the plurality of undesired oral health characteristics on the user interactive display, wherein the user interactive display displays a second advice or instructions for remedying the second one of the plurality of undesired oral health characteristics in response to the selection of the second one of the plurality of undesired oral health characteristics.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIG. 5 is an illustrative screen shot of a displayed web page providing a representation of the health profile.

DETAILED DESCRIPTION OF THE INVENTION

The following detailed description refers to the accompanying drawings. The same reference numbers in different figures identify the same or similar elements.

Figure 1:
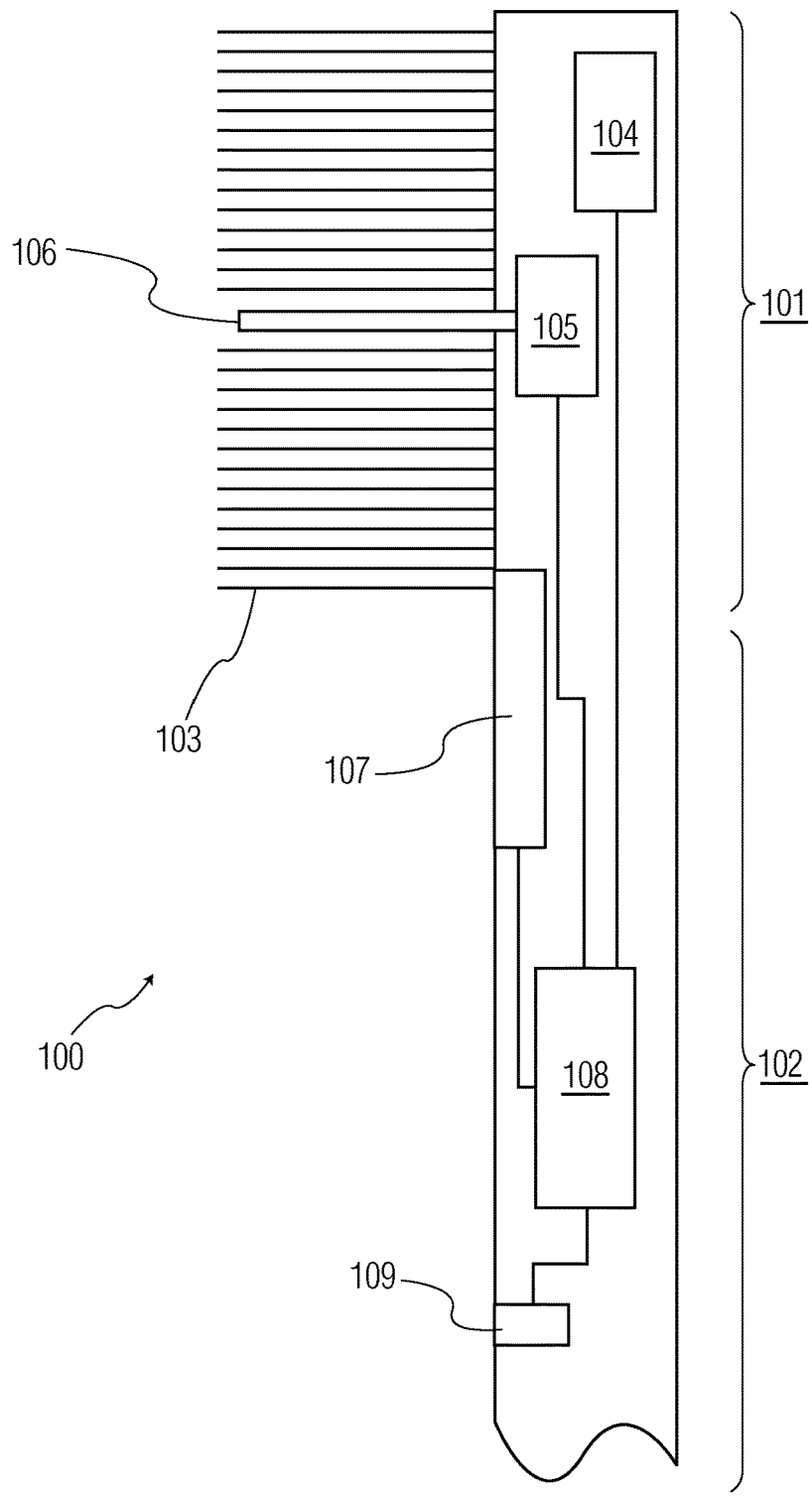
FIG. 1 is a side, cross-sectional view of a top portion of an illustrative toothbrush having one or more sensors.

FIG. 1 illustrates the top portion of an illustrative oral care implement, such as a toothbrush 100. As illustrated, the toothbrush 100 has a head 101 and a handle 102. The head 101 may include an oral care region comprising one or more tooth cleaning elements 103, such as bristles. The head 101 and handle 102 may be made from any desired material, such as rigid plastics, resins, rubber, etc., such as polypropylene.

As used herein, the term "tooth cleaning element" or "cleaning element" includes any type of structure that is commonly used or is suitable for use in providing oral health benefits (e.g., tooth cleaning, tooth polishing, tooth whitening, massaging, stimulating, etc.) by making contact with portions of the teeth and gums. Such tooth cleaning elements include but are not limited to tufts of bristles that can be formed to have a number of different shapes and sizes and elastomeric cleaning members that can be formed to have a number of different shapes and sizes, or a combination of both tufts of bristles and elastomeric cleaning members.

The toothbrush 100 may include a number of additional components to provide features for improved oral care. For example, the toothbrush 100 may include a position sensor 104. The position sensor 104 may be any desired device that can be used to detect a position (or orientation) of the toothbrush 100. For example, the position sensor 104 may be a single- or multi-axis (e.g., 2-D or 3-D) accelerometer, and may be of any desired accelerometer type (e.g., piezoelectric, capacitive or inductive, optical, etc.). The position sensor 104 may be a single, unitary component, or it may include multiple devices, such as multiple accelerometers placed at different orientations. The position sensor 104 may indicate, for example, the angular position with which the user is holding the toothbrush (e.g., 45 degrees with respect to the horizon). The position sensor 104 may also indicate, for example, whether the toothbrush is being held bristle-side up or bristle-side down.

In one illustrative construction, the position sensor 104 may be an accelerometer utilizing Micro-Electronic Mechanical System (MEMS) technology. The position sensor 104 may be embedded in the toothbrush during a molding of toothbrush manufacturing, or may be applied at a later time such as by being in the form of a sticker applied on an exterior of the toothbrush body. A MEMS accelerometer device generates a signal representative of acceleration in a particular direction ("measurement direction"). The MEMS accelerometer detects gravitational force when not being accelerated. Accordingly, different altitudes of the MEMS accelerometer device with respect to the vertical can result in different readings which depend on the coincidence of the measurement direction with the direction of the gravitation pull. The detection of different altitudes may be used to detect the position of the toothbrush and the relative change in position from a first state to a second state, such as from bristle-side to bristle-side down or vice-versa.

The toothbrush 100 may also include a diagnostic sensor or bio-sensor 105. The diagnostic sensor 105 may include one or more individualized sensors or sensor suites to detect various characteristics of a sampled liquid or vapor. For example, the diagnostic sensor 105 may include a sensor configured to detect the pH of the sample, the electrical conductivity or resistivity of the sample, the presence of bacteria in the sample, the presence of certain chemicals in the sample, or any other desired characteristic. These components of the diagnostic sensor 105 may work together to sense whether the sample contains evidence of halitosis, gingivitis, periodontitis, plaque, or any other undesired characteristic. The sensed characteristics need not all be undesirable, either. For example, the diagnostic sensor 105 may be configured to detect the presence of flavonoid alcohols, oils or flavors, which may be indicative of the user having fresh or "good" smelling breath, or that the user has sufficiently brushed with a proscribed dentifrice.

In one construction, the diagnostic sensor 105 is configured to obtain a liquid or vapor sample for its sensing function. For example, the toothbrush 100 may include one or more channel bristles 106, which may be hollow tubes (e.g., including a lumen) that allow liquid and/or vapors to pass, such as oral fluids (e.g., saliva or breath). The channel bristles 106 may be coupled to the diagnostic sensor 105 to provide the sample. The channel bristles 106 may rely simply on capillary action and the motion of brushing to convey the sample, or the toothbrush 100 may include pumps and/or other structures (not illustrated) to draw samples in and to purge the samples when the sensing is completed. Alternative configurations can be used as well. For example, the diagnostic sensor 105 may simply have a portion exposed directly to an outer surface of the toothbrush 100, such that sampling can occur simply by the toothbrush 100 coming into contact with the liquid and/or vapor to be sampled. One example of a commercially available diagnostic sensor using MEMS microfluidics technology is provided by STMicroelectronics of Geneva Switzerland, such as its IN-CHECK platform. This particular system is based on a silicon chip that integrates various functions including microfluidic handling, a miniaturized Polymerase Chain Reaction (PCR) reactor and a microarray. As one skilled in art would understand, PCR can be used to detect oral care pathogens linked to halitosis, gingivitis, and periodontitis, for example. Nevertheless, other diagnostic sensors can be used, such as a pH sensor.

The toothbrush 100 may also include one or more pressure sensors 107. The pressure sensor 107 may be configured to detect the amount of pressure or force that the user is using when brushing his/her teeth. Any type of pressure sensor 107 may be used. For example, a stress/strain type of piezoelectric sensor may be placed at a neck portion (an area where the head 101 and handle 102 meet) to measure how far the head 101 bends during brushing.

The various sensors 104, 105, 107 described above may be electrically or communicatively coupled to a processor 108. The processor 108 generally handles the information gathered by the sensors 104, 105, 107, and reports an analysis of that information to the user, to help inform the user of the conditions within his/her mouth. For example, the toothbrush 100 processor 108 may report that it has detected a higher than normal level of plaque in the upper-left portion of the user's teeth. Additional details of the processor 108, and its operation, are found further below.

The toothbrush 100 may also include one or more input/output (I/O) interfaces 109. The I/O interface 109 may contain any type of electrical interface used to provide data to, or retrieve data from, the processor 108. The I/O interface 109 may be a plug-in physical connection, such as those used for radio headsets, Universal Serial Bus (USB), IEEE-1319 Fire Wire, or any other wired interface. Alternatively, or additionally, the interface 109 may include wireless capabilities, such as Bluetooth or IEEE 802.11 wireless interfaces and associated components. In yet another construction, toothbrush 100 may be a ZIGBEE complaint device. ZIGBEE pertains to an industry specification for a suite of communication protocols using small, low-power digital radio based on the IEEE 802.15.4 standard for wireless personal area networks which is incorporated by reference herein. The radio-controlled configuration may include a transmitter and receiver operating at 2.4 GHz, but other frequencies may be implemented in different geographic regions. The data transfer rates can be 250 Kbs, but other data rates slightly lower or higher could be used. Various commercially available ZIGBEE compliant modules could be implemented. Other known wireless transmission protocols or wireless medium arrangements also can be employed. These interfaces may be used to transmit data, such as the reports discussed below, to an external computing device, such as a personal computer or an Internet web server, as will be discussed further below.

Other components may also be included on the toothbrush 100. For example, a digital display (not shown) may be placed on the toothbrush to assist in reporting output. The display may include light-emitting diode (LED) displays, an alphanumeric display screen, individual lights, or any other desired form of visual output. For example, the display may be an organic LED (or array thereof) that can be tuned to provide a desired luminescent characteristic such as color, temperature, intensity etc. OLED technology can be embedded into the toothbrush molding, or can be applied to the surface of the toothbrush body. It should be understood by those skilled in the art that the present invention is not limited to any particular type of display.

The toothbrush 100 may also include one or more speakers (not shown), to allow the processor 108 to generate audible sounds and tones.

A power source (not shown) for the processor 108 and sensors may also be included. The power source may simply be one or more batteries in a lower portion of the handle 102. Alternative sources, such as solar, motion-based, thermal, etc., may also be used.

Figure 2:
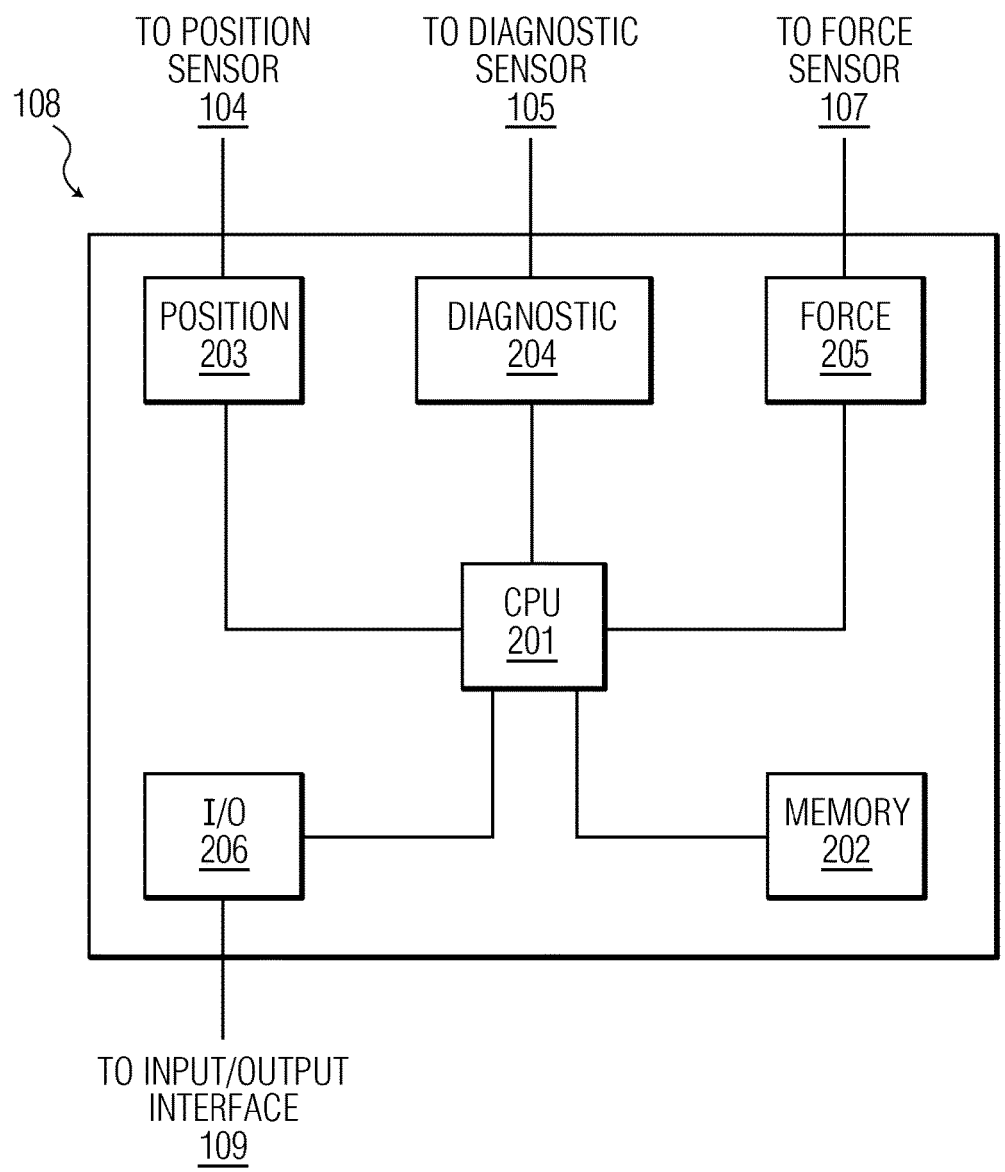
FIG. 2 is an illustrative functional block diagram of the toothbrush of FIG. 1.

FIG. 2 illustrates example components of the processor 108. The processor 108 may be a single integrated circuit (e.g., an application-specific integrated circuit), multiple interconnected circuits, and/or hard-wired circuit logic to perform as described herein. Similarly, the individual components depicted in FIG. 2 may also be integrated, separated or hard-wired as well. The processor 108 may include a central processing unit (CPU) 201, which may be a programmable device or dedicated logic circuit or integrated circuit. The CPU 201 may operate with a memory 202, which may be any type of recordable, computer-readable media. For example, memory 202 may be a static flash memory, dynamic memory, or any other type of electronic storage. In some embodiments, the CPU 201 is a general programmable device, and the memory 202 stores instructions that cause the CPU 201 to perform the various functions described herein.

Those functions include, for example, obtaining information from the various sensors. For example, the processor 108 may have a position sensor interface 203, through which the CPU 201 may communicate with the position sensor 104. The interface may, for example, simply be a pin on an integrated circuit, a wire, or any other desired type of interface, and may vary depending on the type of position sensor chosen. Similarly, the processor 108 may have an I/O interface 206, which can serve as an interface through which the CPU 201 receives and/or transmits data. The lines illustrating wire connections between these components need not be literally as depicted and alternative interconnections may be used.

As mentioned previously, the data output from toothbrush 100 by I/O interface 206 may be provided to an external computing device. This computing device (or a system of computing devices) may use this data to create a health profile of the user of toothbrush 100.

A health profile includes an indication of one or more aspects of the health of an individual. The health aspects may be related to oral health, such as whether the individual has or is suspected of having gingivitis, periodontal gum disease, plaque, and/or halitosis and the like. The health aspects may additionally or alternatively be related to oral-related health indicators, such as whether the individual is, or is suspected of, or is at increased risk of, having heart disease, such as based on the presence of pathogens in the individual's mouth, and/or the individual's body temperature. The health aspects may additionally or alternatively be related to oral care events relating to the use of the toothbrush itself, such as whether the toothbrush is being used properly. For instance, some health aspects may indicate whether a toothbrush was applied with excessive pressure to the teeth or gums, whether the toothbrush was used for a sufficient time in a brushing episode, and/or whether the brushing efficiency was thorough or uneven.

Figure 3:
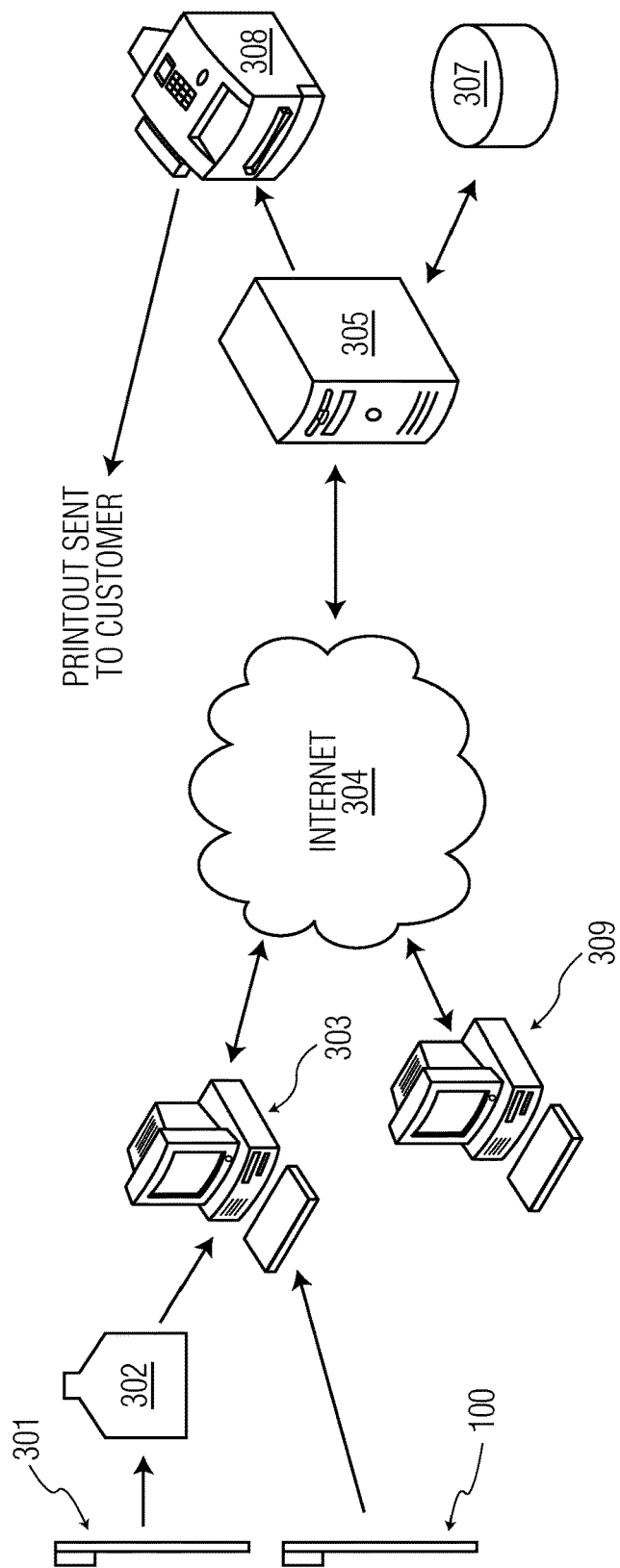
FIG. 3 is a functional block diagram of an illustrative system and process for providing a health profile of a customer from data gathered from the customer's toothbrush.

Referring to FIG. 3, a functional block diagram of an illustrative system and process for providing a health profile of a customer from data gathered from the customer's toothbrush is shown. In this example, a system for providing a health profile may include a first computing device 303, a second computing device 305, and/or a third computing device 309. In addition, one or more of first, second, and third computing devices 303, 305, 309 may include or be coupled with a storage device and/or a printer. In the example shown, computing device 305 is coupled with a storage device 307 and a printer 309.

First, second, and third computing devices 303, 305, 309 may each be any type of computing device, such as one or more laptop computers, desktop computers, personal digital assistants, servers, and/or cellular phones. Each of computing devices 303, 305, 309 may also include a communication interface for sending and/or receiving data to/from a location external to the respective computing device. For example, computing devices 303, 305, 309 may be capable of communicating data back and forth between each other such as via the Internet 304, another type of network such as a cellular and/or landline telephone network, and/or via a direct wired and/or wireless connection.

In operation, information about a toothbrush or other type of oral care implement may be provided to first computing device 303. Two alternative scenarios are shown in FIG. 3. In a first scenario, toothbrush 100 is configured such as shown in FIG. 1. In other words, toothbrush 100 has sensors and a means for outputting data from those sensors. In this case, data may be retrieved from toothbrush 100 (e.g., from I/O interface 206) and sent directly to first computing device 303.

In a second scenario, a toothbrush 301 may be provided that does not have any data output capability. For example, toothbrush 301 may be a conventional toothbrush. In such a case, a chemical and/or biological physical sample may be taken from toothbrush 301 and provided to an analysis processor 302 for analyzing the sample. The sample may include, for example, a portion of toothbrush 301 (or in fact the entirety of toothbrush 301), or a residue disposed on toothbrush 301 that may be removed from toothbrush 301 by any of various means such as by wiping or by dissolving using a solvent. Analysis processor 302 may include, for instance, a silicon chip that integrates the functions of microfluidic handling, a miniaturized PCR reactor, and a microarray. As previously mentioned, PCR can be used to detect oral care pathogens linked to halitosis, gingivitis, and periodontitis, for example. Other diagnostic sensors can additionally or alternatively be used in analysis processor 302, such as a pH sensor. Regardless of how the sample is analyzed in processor 302, the results of processor 302 may be entered (manually or automatically) into first computing device 303.

Figure 4:
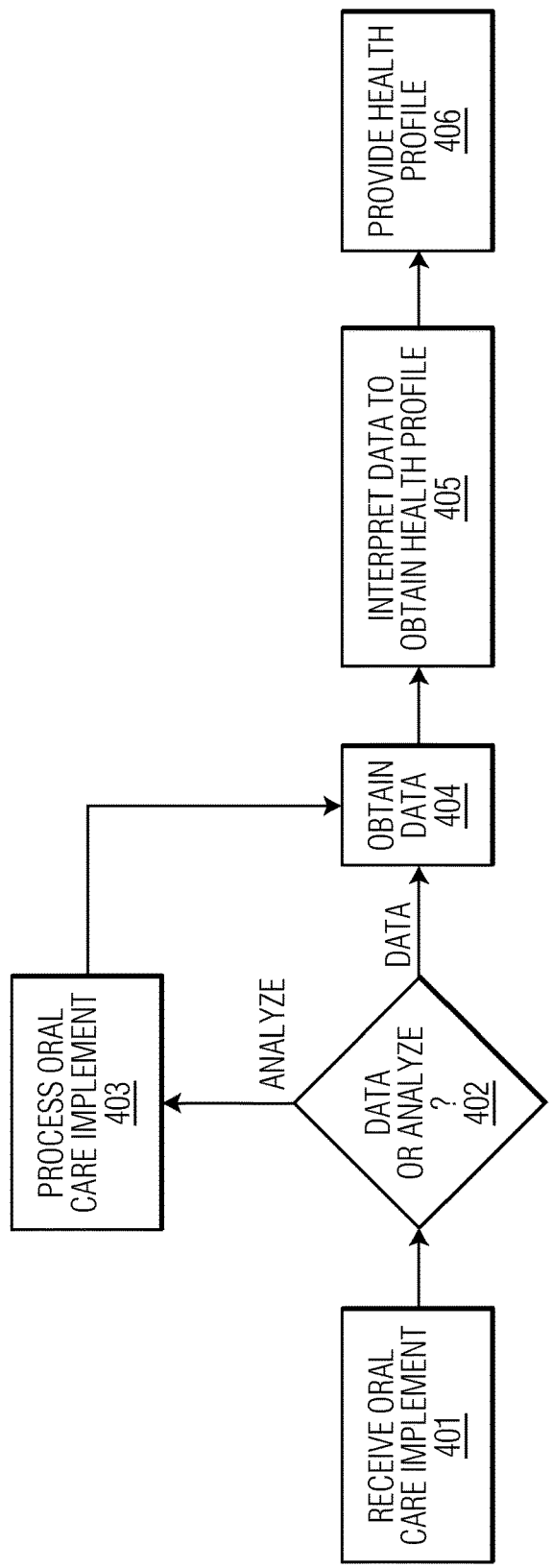
FIG. 4 is a flow chart of illustrative steps that may be performed to provide the health profile.

Referring now to FIG. 4, a flow chart of an illustrative method for providing a health profile of a customer is shown. An oral care implement (such as toothbrush 100 or toothbrush 301) is provided to and used by a customer in step 401. The oral care implement may either be used by the customer at his home, or the customer may go to a service provider where the customer is given the oral care implement to use at the service provider's site. At step 402, the oral care implement is transferred from the customer and received by the service provider. It is determined in step 403 whether the oral care implement is of a type that can provide data or of a type that should be analyzed using processor 302. In either case, data representing information obtained from the toothbrush is inputted to first computing device 303 in step 405.

Returning to the example of FIG. 3, first computing device 303 may process the input data and provide the information represented by the data to second computing device 305 via the Internet 304. Then, second computing device 305 may interpret the received data to create a health profile (step 406 in FIG. 4). The health profile may additionally be stored, such as in storage device 307. Storage device 307 may be any one or more devices suitable for storing data, such as semiconductor memory, hard drives, magnetic tape, optical drives, etc.

Next, the health profile may be output or otherwise made available to a user (step 407 in FIG. 4), such as by displaying a representation of the health profile on a computer display, by providing a displayed representation of the health profile on a website that is made available via the Internet 304, by printing a representation of the health profile on printer 308, and/or by transmitting an electronic mail ("emailing") of a representation of the health profile such as to the user of toothbrush 100 or 301. Where a website provides the health profile, the website may be accessed and viewed by any authorized device such as third computing device 309 running a web browser. Where an email is sent, the email may also be received by third computing device 309.

The present example may be further expanded into a method of providing oral health services. More specifically, a health profile service provider can cater to the public consumer by providing the health profile. For example, computing devices 303 and 305, printer 308, storage device 307, and processor 302 may be owned by or otherwise under the control of the service provider. The toothbrush 100/301 and computing device 309 may be owned by or otherwise under the control of either the service provider or a customer of the service provider. It can be envisioned that such a service provider may provide one or more brick-and-mortar boutiques to which customers may come to use or bring the toothbrushes or other oral care implements for processing and obtaining health profiles. Alternatively, if the toothbrush includes a data output capability, such as toothbrush 100, the customer may provide the data rather than the physical toothbrush for processing. In addition to or as an alternative to brick-and-mortar boutique storefronts, the service provider may operate over the Internet or by mail order such that the customer may upload data via the Internet to the remote business entity, or send the toothbrush to the business entity through the mail.

Alternatively, a private user may own or otherwise exercise control over computing device 303, and also over processor 302. In that context (and in some circumstances in the previously-described service provider context), steps 406 and 407 may be performed by computing device 303 such that the remaining elements 304-309 are not needed.

In general, any of the steps in FIGS. 3 and 4 may be implemented by or assisted by one or more of computing devices 303, 305, and/or 309, such as by programming or otherwise configuring these computing devices with software in the form of computer-executable instructions and/or data stored on a computer-readable medium. The computer-readable medium may include the storage media of any one or more storage devices (such as storage device 307 and/or storage devices inherent to computing devices 303, 305, and 309). As a non-limiting example, a computer-readable medium may include one or more of any of the following in any combination: a computer memory chip, a magnetic disc or tape, or an optical disc.

FIG. 5 shows an example of a displayed representation of a health care profile. This displayed content (i.e., the displayed representation) may be provided by any of computing devices 303, 305, or 309. In some embodiments, the displayed content may be provided on a website or in an email. Where the displayed content is provided on a website, for example, the website may be interactive such that the displayed content changes in response to user selections.

In the example shown in FIG. 5, the displayed content includes an identification of the toothbrush user and/or customer (in this case, "John Q. Doe"), and indications of various aspects of the health profile, including whether or not the following conditions have been detected based on information obtained from toothbrush 100 or 301: periodontal gum disease, gingivitis, plaque, and halitosis (bad breath). In addition, the indicated aspects further include in this example an indication of the brushing pressure experienced by the toothbrush, as well as an indication of the brushing thoroughness experienced by the toothbrush. It will be understood that these aspects are merely illustrative, and that any combination of these and/or other health profile aspects may be indicated. The indicated health aspects may include aspects related to bad health (e.g., the presence of a disease, such as indicated by the presence of a pathogen or the presence or absence of another chemical) and/or aspects related to good health (e.g., the presence of certain desirable flavonoids indicative of the activity of a breath freshener). The aspects of good health and bad health may include, but are not limited to, aspects of good and bad oral health. Bad oral health aspects may include, for example, those aspects associated with oral diseases or with poor oral care practices recognized or otherwise identified by the American Dental Association. Likewise, good oral health aspects may include, for example, those aspects associated with the lack of such oral diseases, or with oral care practices accepted by the American Dental Association.

The displayed content may further include a graphical depiction of an oral cavity divided into multiple different regions. This regional information may be alternatively provided textually rather than graphically. In this case, the various regions are the tongue 501, the upper left quadrant of teeth and/or gums 502, the upper right quadrant of teeth and/or gums 503, the lower left quadrant of teeth and/or gums 504, and the lower right quadrant of teeth and/or gums 505. Other regions may be defined as well. For example, the quadrants 502-505 may be further divided into smaller regions and the tongue 501 may also be subdivided into regions. As another example, the may be only three regions: a tongue region, an upper teeth/gum region, and a lower teeth/gum region. In still another example, there may be no tongue region at all.

Where the display is interactive, the user may select any one of the displayed health aspects to learn more about the selected health aspect. Selection may be performed in any manner desired, such as by the user "clicking" a mouse pointer on the displayed health aspect to be selected, or by using a keyboard to control a selection cursor. In any event, selection of a displayed health aspect may cause the displayed content to provide additional information such as an indication of which of the regions 501-505 of the oral cavity is affected by the selected health aspect (such as by highlighting or otherwise visually distinguishing the affected oral cavity regions), or an indication of recommended products for addressing the health aspect or other advice for dealing with the health aspect. Such products may include, for example, a particular oral care implement or dentifrice. The indication of the particular regions 501-505 may be obtained from data originally generated by position sensor 104 in toothbrush 100, for example.

In the present example as shown in FIG. 5, the health aspect "brushing pressure" has been selected (indicated by the box displayed around this health aspect), which has been indicated as being presently at the "too hard" level (from a selection of "too hard," "medium," and "too soft"). As a result of the user selection, a user-selectable hyperlink to a product for sale that is recommended for assisting the user with proper brushing pressure may be displayed, and/or advice on how to apply proper brushing pressure. It will be understood that user selection of any of the other displayed health aspects may result in a similar set of information customized to the particular selected health aspect.

Also as a result of the user selection of a particular health aspect, an indication of historical values associated with that health aspect may be displayed. For instance, a bar chart 506 or other graphical representation may display previous values or other indications of previous results for that health aspect for the particular user (in this case, for user John Q. Doe). To accomplish this, data representing each user's health profile may be stored (such as in storage device 307) and associated with the respective user, thereby accumulating a health profile history for each user.

In alternative embodiments, information about recommended products for sale, advice about dealing with particular health aspects, indications of oral cavity regions, and/or health profile history may be provided regardless of user selection.

This same information shown on the display of FIG. 5 may be printed on paper by printer 308 and mailed or otherwise provided to the customer or other user of the toothbrush, and/or included in an email to the customer or other user.

While many examples have been discussed with respect to using a toothbrush (such as toothbrushes 100 and 301), the various features and steps described herein may be used in connection with any type of oral care implement having a tooth cleaning element. Also, while the invention has been described with respect to specific examples including presently preferred modes of carrying out the invention, those skilled in the art will appreciate that there are numerous variations and permutations of the above described systems and techniques. Thus, the spirit and scope of the invention should be construed broadly as set forth in the appended claims.

What is claimed is:

1. A method of monitoring oral health comprising:
deriving a health profile of an individual from information obtained from a sample taken from the individual;
displaying a representation of the health profile on an interactive display, wherein the representation of the health profile includes a list of undesirable oral health characteristics that are detectable from the sample and a graphical depiction of an oral cavity divided into a plurality of regions; and
wherein in response to a user selecting a first one of the undesirable oral health characteristics on the interactive display, the graphical depiction of the oral cavity on the interactive display changes to indicate which regions of the individual's oral cavity are affected by the first one of the undesirable oral health characteristics.

2. The method of claim 1, wherein in response to the user selecting the first one of the undesirable oral health characteristics on the interactive display, the graphical depiction of each of the plurality of regions of the oral cavity that are affected by the first one of the undesirable oral health characteristics are visually distinguished on the interactive display from the graphical depiction of the plurality of regions of the oral cavity that are unaffected by the first one of the undesirable oral health characteristics.

3. The method of claim 2, wherein in response to the user selecting the first one of the undesirable oral health characteristics on the interactive display, the graphical depiction of each of the plurality of regions of the oral cavity that is affected by the first one of the undesirable oral health characteristics is highlighted on the interactive display.

4. The method of claim 1 wherein the list of undesirable oral health characteristics comprises one or more of periodontal gum disease, gingivitis, plaque, halitosis, and heart disease.

5. The method of claim 1, wherein the representation of the health profile is displayed as content on an interactive website and the content changes in response to the user selecting different ones of the undesirable oral health characteristics.

6. The method of claim 1, wherein in response to the user selecting a second one of the undesirable oral health characteristics, the representation of the health profile on the interactive display changes to indicate which regions of the individual's oral cavity are affected by the second one of the undesirable oral health characteristics.

7. The method of claim 1, wherein the sample is a liquid or vapor taken from the individual's saliva or breath.

8. The method of claim 7 wherein the information is obtained from an oral care implement that comprises the sample, the oral care implement configured to detect each of the undesirable oral health characteristics on the list.

9. The method of claim 8, wherein the oral care implement comprises a toothbrush.

10. The method of claim 8, wherein the oral care implement comprises a diagnostic sensor configured to detect at least one of pH, electrical conductivity, electrical resistivity, or the presence of bacteria in the individual's saliva or breath.

11. The method of claim 10, wherein the oral care implement further comprises a channel bristle coupled to the diagnostic sensor, the channel bristle being hollow to enable the individual's saliva or breath to come into contact with the diagnostic sensor.

12. The method of claim 10, wherein the diagnostic sensor is exposed directly to an outer surface of the oral care implement.

13. A method of monitoring oral health comprising:
deriving a health profile of an individual from information obtained from a sample taken from the individual;
displaying a representation of the health profile on a user interactive display, wherein the representation of the health profile includes a list of a plurality of undesirable oral health characteristics that are detectable from the sample;

selecting a first one of the plurality of undesirable oral health characteristics on the user interactive display, wherein the user interactive display changes to display a first advice or instructions for remedying the first one of the plurality of undesirable oral health characteristics in response to the selection of the first one of the plurality of undesirable oral health characteristics; and selecting a second one of the plurality of undesirable oral health characteristics on the user interactive display, wherein the user interactive display changes to display a second advice or instructions for remedying the second one of the plurality of undesirable oral health characteristics in response to the selection of the second one of the plurality of undesirable oral health characteristics;

wherein the second one of the plurality of undesirable oral health characteristics is different from the first one of the plurality of undesirable oral health characteristics; and wherein the representation of the health profile further includes a graphical depiction of an oral cavity divided into different regions, and wherein the different regions of the graphical depiction of the oral cavity that correspond to a region of the user's oral cavity that is affected by the first one of the plurality of undesirable oral health characteristics is highlighted in response to the selection of the first one of the plurality of undesirable oral health characteristics.

14. The method of claim 13 wherein one of the plurality of undesirable oral health characteristics is selected from brushing pressure and brushing thoroughness.

15. The method of claim 13, wherein upon selecting the second one of the plurality of undesirable oral health characteristics on the user interactive display, the user interactive display no longer displays the first advice or instructions for remedying the first one of the plurality of undesirable oral health characteristics.

16. The method of claim 13 wherein the first advice or instructions is a recommendation to use a first product to remedy the first undesirable oral health characteristic and wherein the second advice or instructions is a recommendation to use a second product to remedy the second undesirable oral health characteristic.

17. The method of claim 13, wherein the first one of the plurality of undesirable oral health characteristics is a first one of periodontal gum disease, gingivitis, plaque, halitosis, and heart disease and wherein the second one of the plurality of undesirable oral health characteristics is a second different one of periodontal gum disease, gingivitis, plaque, halitosis, and heart disease.

18. The method of claim 13 wherein the information is obtained from an oral care implement that comprises the sample, the oral care implement configured to detect each of the undesirable oral health characteristics on the list.

19. The method of claim 18, wherein the oral care implement comprises a toothbrush.

* * * * *